United States Patent
Ierulli

(10) Patent No.: US 10,149,781 B2
(45) Date of Patent: Dec. 11, 2018

(54) NASAL DILATOR WITH DECORATIVE DESIGN ELEMENT

(71) Applicant: Joseph V. Ierulli, Portland, OR (US)

(72) Inventor: Joseph V. Ierulli, Portland, OR (US)

(73) Assignee: CORBETT LAIR INC., Brandenton, FL (US)

( * ) Notice: Subject to any disclaimer, the term of this patent is extended or adjusted under 35 U.S.C. 154(b) by 458 days.

(21) Appl. No.: 14/623,918

(22) Filed: Feb. 17, 2015

(65) Prior Publication Data

US 2015/0230966 A1  Aug. 20, 2015

Related U.S. Application Data

(60) Provisional application No. 61/941,761, filed on Feb. 19, 2014.

(51) Int. Cl.
 *A61F 5/08* (2006.01)
 *B29L 31/00* (2006.01)

(52) U.S. Cl.
 CPC ............ *A61F 5/08* (2013.01); *B29L 2031/753* (2013.01)

(58) Field of Classification Search
 CPC .............................. B29L 2031/753; A61F 5/08
 See application file for complete search history.

(56) References Cited

U.S. PATENT DOCUMENTS

| | | |
|---|---|---|
| 5,476,091 A | 12/1995 | Johnson |
| 5,479,944 A | 1/1996 | Petruson |
| 5,533,499 A | 7/1996 | Johnson |
| 5,533,503 A | 7/1996 | Doubek et al. |
| 5,546,929 A | 8/1996 | Muchin |
| 5,549,103 A | 8/1996 | Johnson |
| RE35,408 E | 12/1996 | Petruson |
| 5,611,333 A | 3/1997 | Johnson |
| 5,653,224 A | 8/1997 | Johnson |
| 5,706,800 A | 1/1998 | Cronk et al. |
| 5,718,224 A | 2/1998 | Muchin |
| 5,769,089 A | 6/1998 | Hand et al. |
| 5,890,486 A | 4/1999 | Mitra et al. |
| 5,931,854 A | 8/1999 | Dillon |
| 5,957,126 A | 9/1999 | Neeser |
| 6,006,746 A | 12/1999 | Karell |
| 6,029,658 A | 2/2000 | De Voss |
| 6,058,931 A | 5/2000 | Muchin |
| 6,065,470 A | 5/2000 | Van Cromvoirt et al. |
| 6,098,616 A | 8/2000 | Lundy et al. |

(Continued)

FOREIGN PATENT DOCUMENTS

| | | |
|---|---|---|
| EP | 855175 A1 | 7/1998 |
| ES | 289561 | 10/1985 |

*Primary Examiner* — Son Dang
(74) *Attorney, Agent, or Firm* — Mersenne Law

(57) ABSTRACT

The present invention integrates a decorative design element into the functional elements of a nasal dilator. The design element includes a predetermined artistic, aesthetic, shape defined by at least a portion of a periphery of at least one layer of the dilator. The nasal dilator thus may decoratively express or represent teams, programs, sports, organizations, sponsors, institutions, clubs, schools, companies, product or service brands, legal entities, individuals, etc. In use the nasal dilator stabilizes and/or expands the nasal outer wall tissues and prevents said tissues from drawing inward during breathing.

8 Claims, 17 Drawing Sheets

(56) References Cited

U.S. PATENT DOCUMENTS

| | | |
|---|---|---|
| 6,196,228 B1 | 3/2001 | Kreitzer et al. |
| 6,244,265 B1 | 6/2001 | Cronk et al. |
| 6,276,360 B1 | 8/2001 | Cronk et al. |
| 6,318,362 B1 | 11/2001 | Johnson |
| 6,357,436 B1 | 3/2002 | Kreitzer et al. |
| 6,375,667 B1 | 4/2002 | Ruch |
| 6,453,901 B1 | 9/2002 | Ierulli |
| 6,470,883 B1 | 10/2002 | Beaudry |
| 6,550,474 B1 | 4/2003 | Anderson et al. |
| 6,694,970 B2 | 2/2004 | Spinelli et al. |
| 6,769,428 B2 | 8/2004 | Cronk et al. |
| 6,769,429 B1 | 8/2004 | Benetti |
| 7,067,710 B1 | 6/2006 | Beaudry |
| 7,114,495 B2 * | 10/2006 | Lockwood, Jr. .......... A61F 5/08 128/200.24 |
| D639,762 S | 6/2011 | Brogden et al. |
| D644,325 S | 8/2011 | Brunner et al. |
| D644,324 S | 10/2011 | Brunner et al. |
| 8,047,201 B2 | 11/2011 | Guyuron et al. |
| 8,062,329 B2 | 11/2011 | Ierulli |
| D651,710 S | 1/2012 | Brogden et al. |
| 8,115,049 B2 | 2/2012 | Beaudry |
| D659,245 S | 5/2012 | Ierulli |
| 8,188,330 B2 | 5/2012 | Beaudry |
| D662,203 S | 6/2012 | Smith |
| D667,543 S | 9/2012 | Ierulli |
| D671,643 S | 11/2012 | Ierulli |
| D672,461 S | 12/2012 | Brogden et al. |
| D672,872 S | 12/2012 | Brunner et al. |
| D673,270 S | 12/2012 | Brunner et al. |
| 8,342,173 B2 * | 1/2013 | Lockwood, Jr. .......... A61F 5/08 128/200.24 |
| 8,444,670 B2 | 5/2013 | Ierulli |
| 8,584,671 B2 | 11/2013 | Ierulli |
| 8,616,198 B2 | 12/2013 | Guyuron et al. |
| 8,617,199 B2 | 12/2013 | Eull et al. |
| 8,641,852 B2 | 2/2014 | Ierulli |
| D707,814 S | 6/2014 | Ierulli |
| D707,815 S | 6/2014 | Ierulli |
| 8,834,511 B2 | 9/2014 | Holmes et al. |
| 8,834,512 B1 | 9/2014 | Brown et al. |
| 8,834,514 B2 | 9/2014 | Smith |
| 8,858,587 B2 | 10/2014 | Ierulli |
| D722,161 S | 2/2015 | Reyers |
| D722,162 S | 2/2015 | Reyers |
| D725,772 S | 3/2015 | Ierulli |
| D725,773 S | 3/2015 | Ierulli |
| 9,095,422 B2 | 8/2015 | Gray |
| D738,496 S | 9/2015 | Peck |
| D739,015 S | 9/2015 | Martin |
| 9,119,620 B2 | 9/2015 | Peterson et al. |
| D741,997 S | 10/2015 | Ierulli |
| D741,998 S | 10/2015 | Martin |
| D743,544 S | 11/2015 | Ierulli |
| D743,545 S | 11/2015 | Ierulli |
| D743,565 S | 11/2015 | Engel et al. |
| D745,147 S | 12/2015 | Ierulli |
| 9,204,988 B1 | 12/2015 | Fischell |
| D746,982 S | 1/2016 | Ierulli |
| D747,478 S | 1/2016 | Brunner et al. |
| D753,294 S | 4/2016 | Guyuron et al. |
| D755,376 S | 5/2016 | Ierulli |
| D758,575 S | 6/2016 | Ierulli |
| D758,576 S | 6/2016 | Ierulli et al. |
| D759,240 S | 6/2016 | Ierulli |
| D759,241 S | 6/2016 | Ierulli |
| D759,242 S | 6/2016 | Ierulli |
| 9,364,367 B2 | 6/2016 | Ierulli |
| 9,364,368 B2 | 6/2016 | Ierulli |
| 9,381,332 B2 | 7/2016 | Judd |
| D764,055 S | 8/2016 | Ierulli et al. |
| D764,662 S | 8/2016 | Ierulli et al. |
| 9,414,957 B1 | 8/2016 | Fischell |
| 9,427,945 B2 | 8/2016 | Gray et al. |
| D779,666 S | 2/2017 | Ierulli et al. |
| D779,667 S | 2/2017 | Ierulli et al. |
| 9,566,183 B1 | 2/2017 | Fischell |
| 2008/0058858 A1 | 3/2008 | Smith |
| 2008/0097517 A1 | 4/2008 | Holmes et al. |
| 2008/0257341 A1 * | 10/2008 | Ierulli ................... A61F 5/08 128/200.24 |
| 2009/0125052 A1 | 5/2009 | Pinna et al. |
| 2009/0234383 A1 * | 9/2009 | Ierulli ................... A61F 5/08 606/204.45 |
| 2010/0210988 A1 | 8/2010 | Dallison |
| 2010/0298861 A1 | 11/2010 | Fenton |
| 2011/0000483 A1 | 1/2011 | Matthias et al. |
| 2011/0054517 A1 | 3/2011 | Holmes et al. |
| 2011/0166594 A1 | 7/2011 | Eull |
| 2011/0224717 A1 | 9/2011 | Lockwood |
| 2012/0004683 A1 * | 1/2012 | Gray ..................... A61F 5/08 606/204.45 |
| 2012/0022582 A1 | 1/2012 | Guyuron |
| 2012/0067345 A1 | 3/2012 | Shilon |
| 2012/0172923 A1 | 7/2012 | Fenton |
| 2012/0209313 A1 | 8/2012 | Ierulli |
| 2012/0232455 A1 | 9/2012 | Beaudry |
| 2013/0104882 A1 * | 5/2013 | Ierulli ................... A61F 5/08 128/200.24 |
| 2013/0118488 A1 | 5/2013 | Ledogar |
| 2014/0194922 A1 | 7/2014 | Ierulli |
| 2014/0148844 A1 | 10/2014 | Andre |
| 2014/0296904 A1 | 10/2014 | Andre |
| 2014/0350596 A1 | 11/2014 | Smith |
| 2015/0005812 A1 | 1/2015 | Holmes |
| 2015/0012035 A1 | 1/2015 | Ierulli |
| 2015/0051636 A1 * | 2/2015 | Lockwood, Jr. .......... A61F 5/08 606/199 |
| 2015/0090398 A1 | 4/2015 | Ierulli |
| 2015/0090399 A1 | 4/2015 | Ierulli |
| 2015/0094757 A1 | 4/2015 | Ierulli |
| 2015/0094758 A1 | 4/2015 | Ierulli |
| 2015/0216709 A1 | 8/2015 | Peck |
| 2015/0230966 A1 | 8/2015 | Ierulli |
| 2015/0250637 A1 | 9/2015 | Ierulli |
| 2015/0290021 A1 | 10/2015 | Gray |
| 2015/0359654 A1 | 12/2015 | Bentivegna et al. |
| 2016/0008161 A1 | 1/2016 | Ierulli et al. |
| 2016/0278967 A1 | 9/2016 | Ierulli |
| 2016/0278968 A1 | 9/2016 | Ierulli |
| 2016/0339619 A1 | 11/2016 | Gray |

* cited by examiner

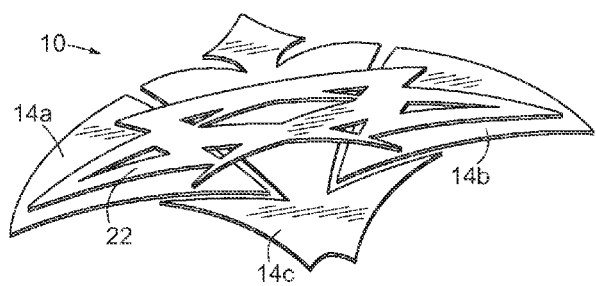
FIG. 9
FIG. 8
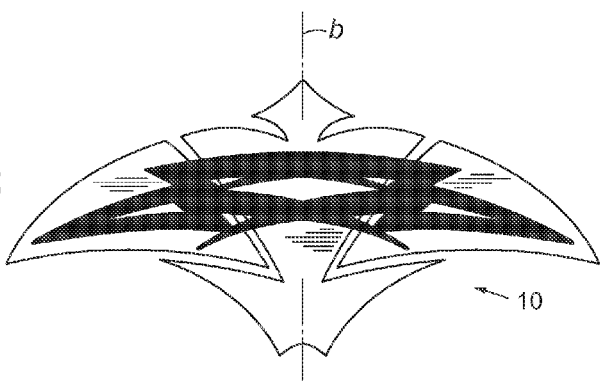
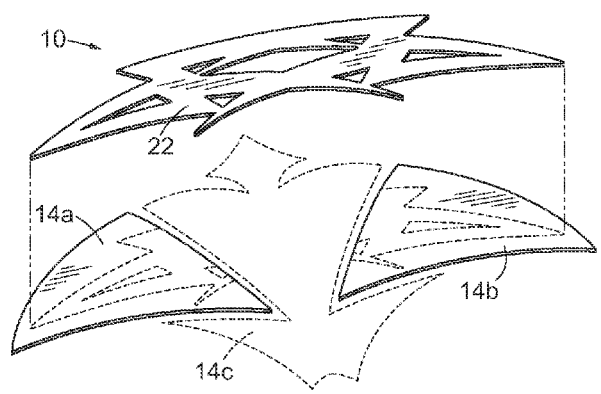
FIG. 10
FIG. 11
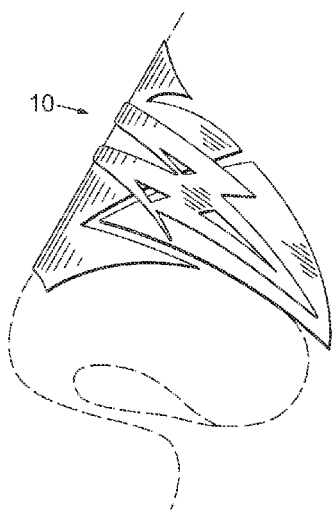
FIG. 12

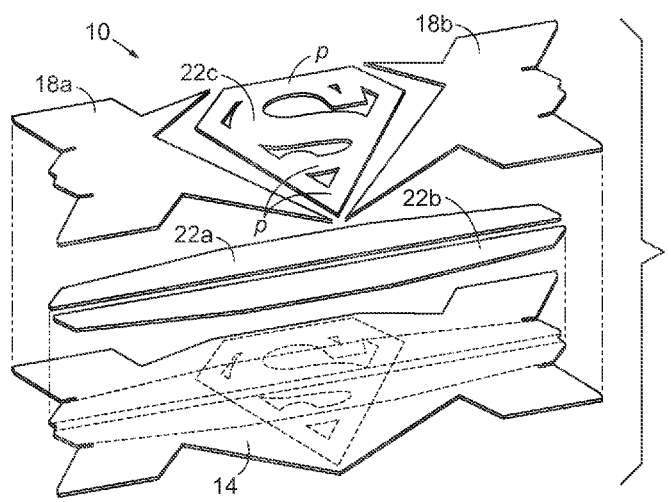
FIG. 29
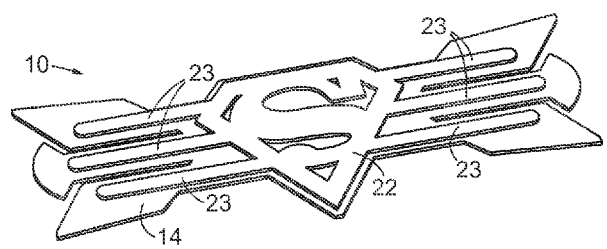
FIG. 31
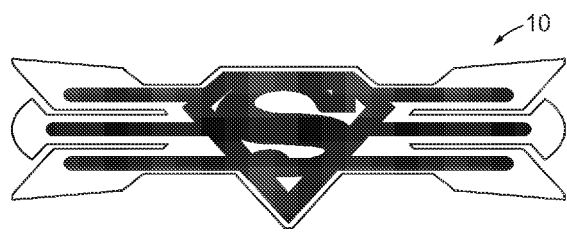
FIG. 30
FIG. 32
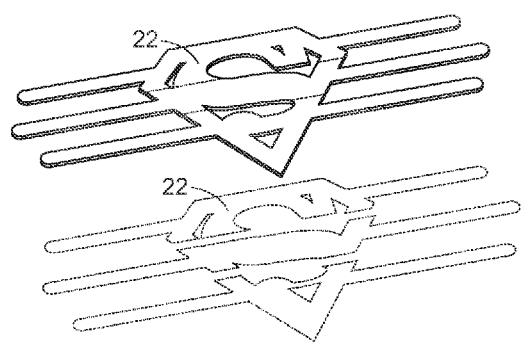

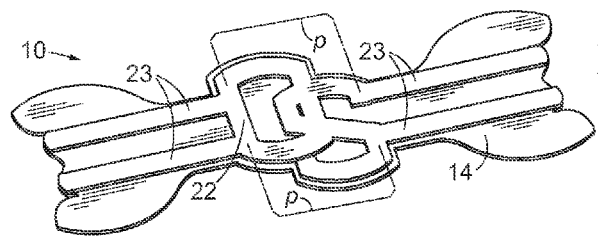
FIG. 38
FIG. 37
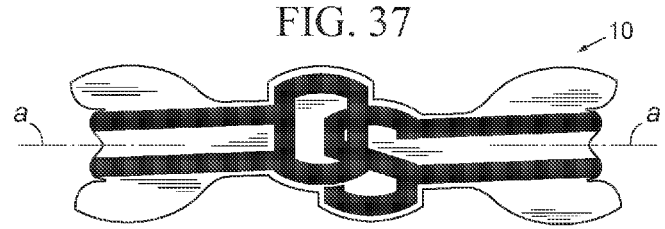
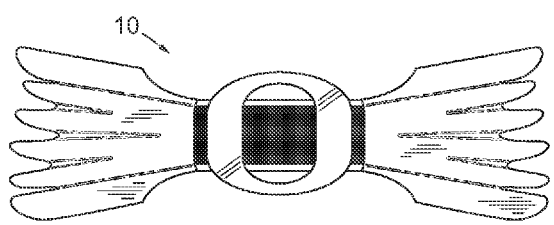
FIG. 39
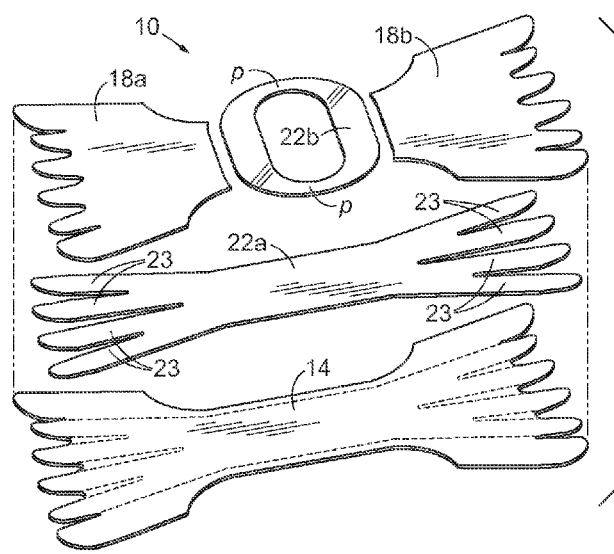
FIG. 41

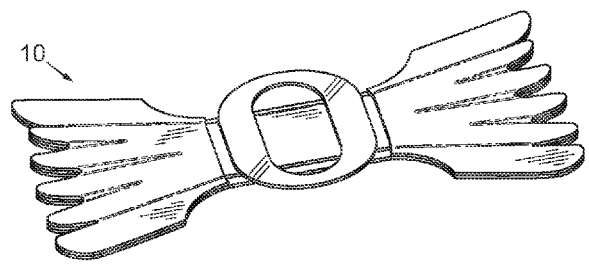
FIG. 40
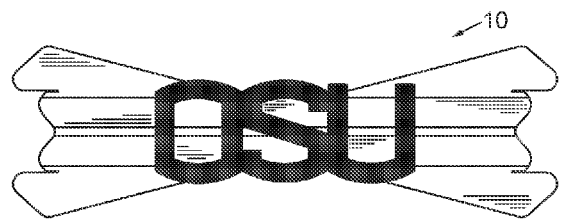
FIG. 42
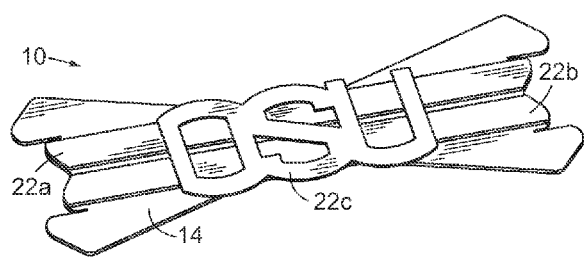
FIG. 43
FIG. 44
FIG. 45
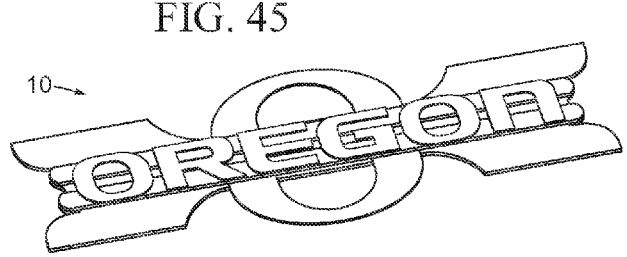

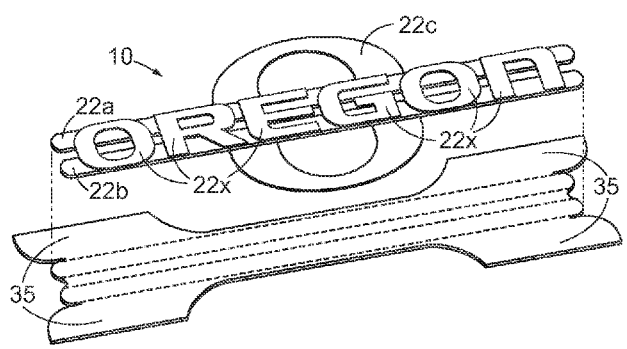
FIG. 46
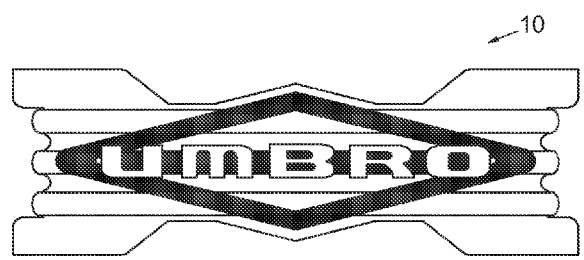
FIG. 47
FIG. 48
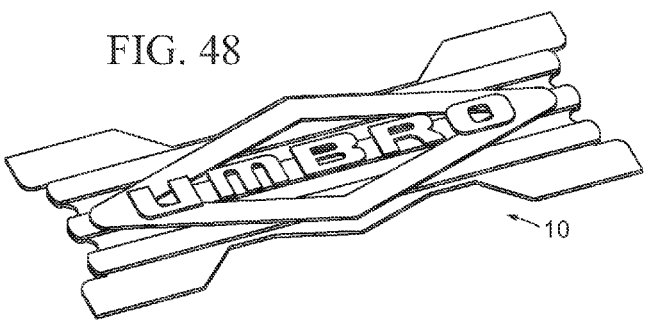
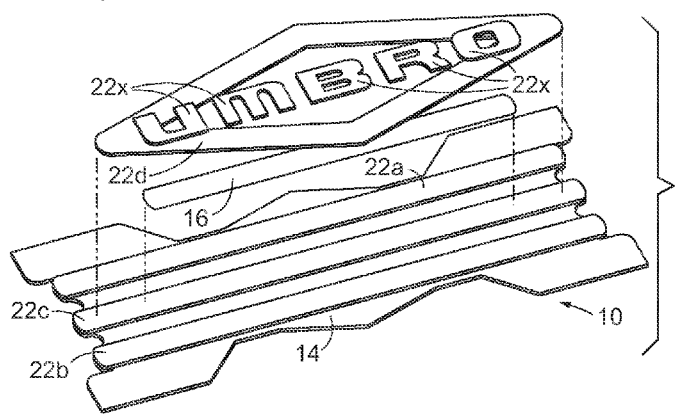
FIG. 49

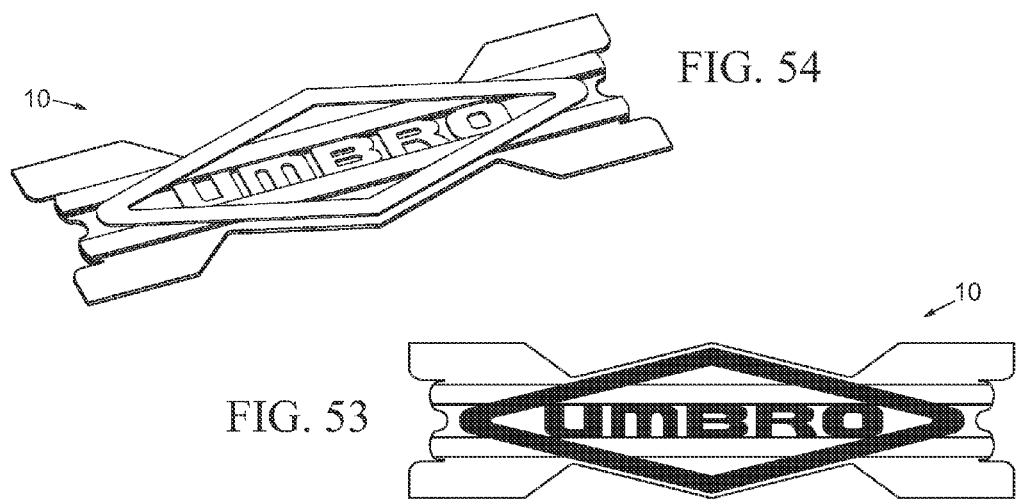
FIG. 54
FIG. 53
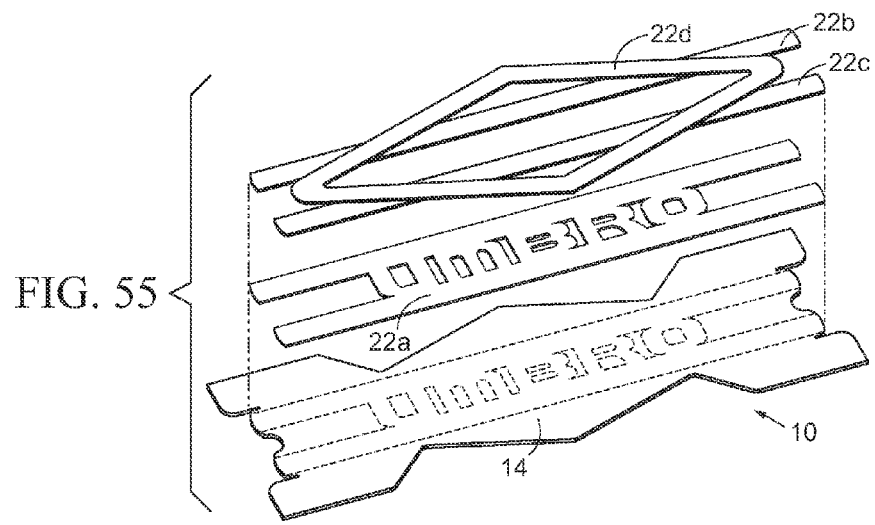
FIG. 55
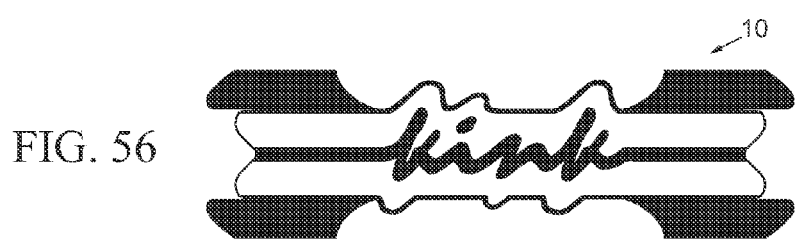
FIG. 56

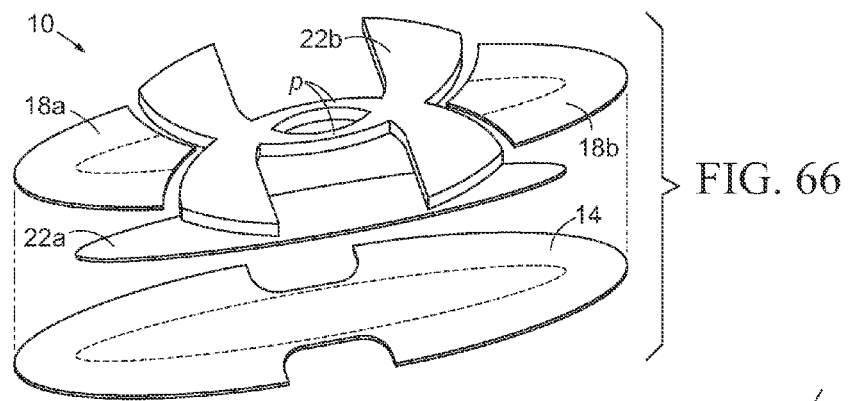
FIG. 66
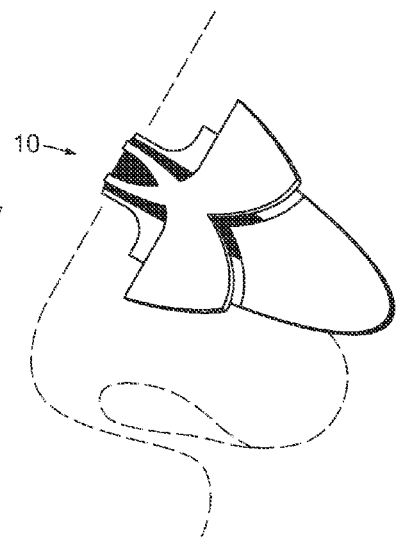
FIG. 67
FIG. 64
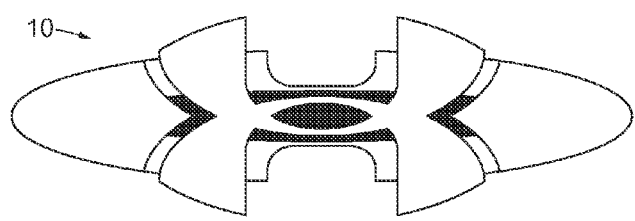
FIG. 65
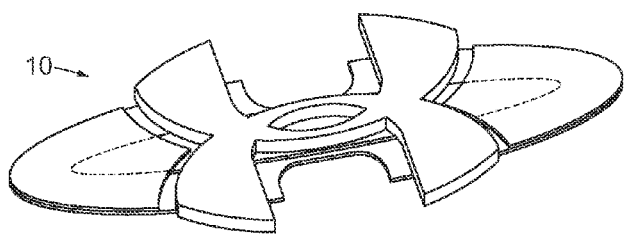

FIG. 69
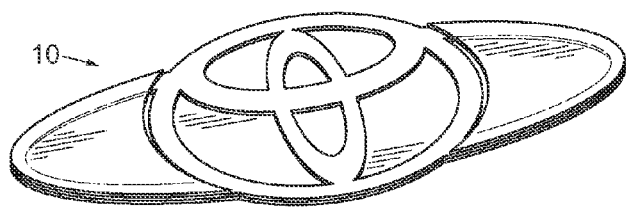
FIG. 68
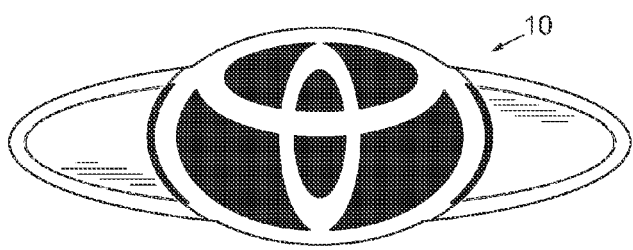
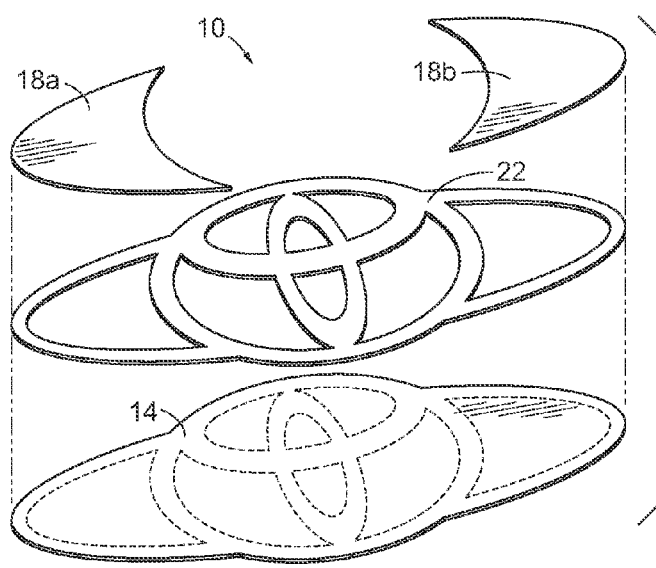
FIG. 70

NASAL DILATOR WITH DECORATIVE DESIGN ELEMENT

RELATED APPLICATIONS

The present application claims priority benefit to U.S. Provisional Patent Application No. 61/941,761 filed 19 Feb. 2014.

FIELD OF THE INVENTION

The present invention relates generally to medical devices, and more specifically to apparatus for, and methods of, supporting, stabilizing or dilating external tissue of the human body. As disclosed and taught in the preferred embodiments, the tissue dilator devices are particularly suitable for, and are directed primarily to, external nasal dilators used in supporting, stabilizing and dilating outer wall tissues of the nasal airway passages of the human nose.

The United States Food and Drug Administration classifies the external nasal dilator as a Class I Medical Device. External nasal dilators provided to consumers in the retail marketplace are more commonly known as nasal strips. Embodiments for nasal strips disclosed herein are directed primarily to use by human athletes and non-athletes.

BACKGROUND OF THE INVENTION

External nasal dilators worn on the skin surface of the human nose are well disclosed in the art. In use the external nasal dilator is flexed across the bridge of the nose, engaging the nasal passage outer wall tissues on each side of the bridge, and held thereto by adhesive. A resilient member (synonymously referred to in the art as a spring, spring member, resilient band, resilient member band, spring band, or bridge) extends along the length of the device, secured to a thin, flexible sheet or sandwiched between two thin flexible sheets. Flexed across the bridge of the nose, the resilient member, having resiliency or resilient properties, exerts spring biasing forces that urge the nasal outer wall tissues outward, stabilizing, expanding dilating the nasal passageways. Stabilized or dilated tissue reduces nasal airflow resistance within the nasal passages, promoting a corresponding increase, ease, or improvement in nasal breathing.

Nasal dilators having a decoration imprinted thereon are disclosed in U.S. Pat. Publication No. 2009-0234383 A1 (Ierulli, FIGS. 10-13), and U.S. Pat. No. 6,375,667 (Muchin). These disclosures teach decoration by imprinting a logo or design, such as by ink using conventional means, onto a visible flat surface of a resilient member. However, the decoration is separate from, and forms no part of, the dilator's function and utility.

There is a continuing need in the art to develop nasal dilator devices adapted for use by athletes, and to integrate fan support for athletics, athletes, sports teams, and sports in general. The relationship between fans and sports may similarly exist, for example, in popular culture, or between organizations, companies, institutions and other entities, etc., and their supporters, followers, employees, customers or enthusiasts. The present invention provides unique and novel nasal dilator devices that address these market needs.

SUMMARY OF THE INVENTION

The present invention comprises resilient and engagement elements and a decorative design element. An additional directional element may affect, alter or improve the resilient and engagement functions. The engagement element functions primarily to affix, adhere, secure or engage the article to external tissue. The resilient element comprises a resilient member structure in at least one resilient layer. The decorative design element conveys a desired artistic expression and contributes, at least in part, and preferably substantially, to the resilient or engagement functions.

Engagement, resilient, directional, and decorative design elements are defined by at least a portion of at least one layer, member or component of the dilator. Any layer may overlap or overlay any other layer in whole or in part. The peripheral dimensions of the dilator may be defined, in whole or part, by an element thereof, or by a layer or portion thereof, or by any combination of layers.

The present invention integrates, combines and incorporates the decorative design element with, and into, the functional utility of the nasal dilator. Rather than imprinting a design or logo onto a material from which a medical device, such as a nasal dilator, is fabricated, the components (layers or members) of the present invention, either separately or combined, are instead peripherally shaped to form a predetermined decorative design. The peripherally shaped layer or member functions as the engagement and/or resilient element of the dilator, the decorative design element thus integrated therewith, as illustrated and described herein. For example, a shaped resilient layer may be secured atop a complementary-shaped base layer. The decorative design element provides more of a three-dimensional appearance that is generally possible with traditional imprinting. Using color or imprinting may enhance the design or allow it to be more specific to a particular entity or individual, but its basic shape, periphery, surface area, dimensions, configuration, etc., are primarily determined by at least some of the dilator's constituent parts.

The decorative design element may comprise at least one of a shaped character, letter, symbol, title, crest, logo, emblem, mark, indicia, artistic rendering, graphic, decoration, representation, acronym, word, phrase, message, expression, or the like. The decorative design element or a portion thereof may be generically referred to herein as a shaped design. The present invention may be adapted for use by athletes and non-athletes, and may decoratively express or represent teams, programs, sports, organizations, sponsors, institutions, clubs, schools, companies, product brand, service brand, corporate brand, legal entities, celebrities, actors, individuals, etc. Nasal dilators adapted for use by athletes may include greater resiliency than those adapted for use by non-athletes.

The decorative design element may be configured to provide support for, or a relationship between, individuals and organized entities. Nasal dilators of the present invention are adapted for athletic or non-athletic use. It will be apparent to those skilled in the art that the design element may be similarly incorporated to other medical devices or consumer products, particularly those made from the same class of materials as external nasal dilators, and fabricated, or converted, in substantially the same manner.

Nasal dilators of the present invention are capable of resilient deformation by virtue of the resilient element being substantially rigid in-plane and being flexible out-of-plane. When released after being flexed across the bridge of the nose, the dilator returns to a substantially planar or pre-flexed state. In use the dilator stabilizes the outer wall of the nasal passages and prevents the tissue thereof from drawing inward during breathing, and may further expand, or dilate, the nasal passage outer walls.

To provide stabilization or dilation, the resilient element is preferably configured to generate from about 10 grams to about 35 grams of resiliency, or spring biasing force, for non-athletes, and from about 25 grams to about 45 grams for athletes. Spring biasing force is determined by the type of resilient member material used and the configuration of the resilient member structure, including width, length, and thickness thereof. The resilient element comprises a resilient member structure having at least one resilient member in at least one resilient layer. Two or more resilient members may overlay or overlap one another. A resilient member may include components, such as resilient spring fingers or decorative/functional components, or the resilient member may be bifurcated laterally to form resilient spring fingers.

At least a portion of the resilient element may be peripherally shaped or otherwise configured to render all or part of the predetermined artistic design. Some or all of the shaping itself may be configured without regard, or relevance, to resilient function. However, the resilient member structure as a whole is configured by its overall dimensions to generate suitable spring biasing force or resiliency as described herein. (The terms spring biasing, spring biasing force, spring force, resiliency, spring constant, etc. as used herein are generally synonymous.)

The directional element modifies, directs, affects or alters dilator spring biasing properties to enhance efficacy, engagement, useful duration, comfort, or ease of use. The directional element includes one or more design features that may, for example: spread spring biasing forces to a greater lateral extent of the dilator; increase or decrease localized spring biasing forces; mitigate or transform delaminating peel and tensile forces, at least in part, from primarily peel forces to primarily shear forces; direct spring biasing forces to discreet engagement contact points; or create lessening of or gradiently reduce spring biasing forces at the device end regions.

Some embodiments of the present invention are configured to function adequately when composed of a resilient element and decorative design element. That is, the directional element may be configured so that a resilient member structure forms the dilator substantially in its entirety; the dilator thus comprising primarily the resilient member structure together with an engagement element, or means, consisting primarily of an adhesive substance.

The decorative design element may be defined by the resilient element or resilient member structure, and may be further defined, or complemented, by the engagement element. The design element may be equally defined by the resilient member structure and the engagement element. Two or more shaped resilient members may be spatially arranged relative to each other so as to form a desired design, in addition to generating a desired functional resiliency. Alternatively, a shaped resilient member may be combined with a conventional resilient member or structure, such as, for example, one or more generally rectangular resilient members, or a single resilient member having a plurality of spring fingers extending outward from a common center. Further alternatively, the decorative design element may be substantially defined by the engagement element together with a conventional resilient member or structure, particularly, for example, when a desired aesthetic shape does not lend itself to a configuration suitable to provide support, stabilization or dilation.

In order to render a desired decorative design, resilient members of the present invention may, of necessity, have areas of material removed from within the peripheral boundaries thereof. U.S. Pat. No. 5,611,333 (Johnson) discloses a resilient member having cuts, notches, openings, slits, etc. formed within the resilient member periphery so as to selectively reduce and achieve a desired spring band resiliency. However, the disclosure does not teach or suggest this configuration as decoration or as a decorative design element of the device.

A non-functional, or substantially non-functional, shaped design or portion thereof may be added to the present invention by, for example, conventional imprinting, or by a material layer shaped and/or colored as desired. Decorative imprinting or coloring, by any conventional means, may be applied to any device layer to enhance or otherwise affect the decorative design element, or to make the shaped design more specific to the entity for which it is intended.

It is the principal objective of the present invention to integrate decorative design elements into novel nasal dilator and tissue support devices, and to provide graphical expression of support for, or a relationship between, individuals and organized entities, such as, for example, professional athletes and fans or supporters thereof. A further objective is to address the dynamic relationship between engagement to the nose during athletic activity and the greater resiliency that may be desirable in nasal dilator devices used by athletes. The present invention builds upon the prior art and discloses new, useful, and non-obvious external nasal dilator and nasal support devices.

The nasal dilators depicted, taught, enabled and disclosed herein represent families of new, useful and non-obvious devices having a variety of alternative embodiments. Dilator elements, layers, members, components, materials, or regions may be of differing size, area, thickness, length, width or shape than that illustrated or described while still remaining within the purview and scope of the present invention.

Some drawing figures depict an element, layer or member in solid black to illustrate contrast between dilator elements or members. Some embodiments of the present invention may refer to, or cross reference, other embodiments. It will be apparent to one of ordinary skill in the art that some features may be applied, interchanged or combined from one embodiment to another.

Broken lines and dashed lines are used in the drawings to aid in describing relationships or circumstances with regard to objects:

A broken line including a dash followed by three short spaces with two short dashes therebetween indicates separation for illustrative purposes, such as in an exploded view, or to indicate an object or objects removed or separated from one or more other objects.

A dashed line (sometimes referred to as a shadow line) of successive short dashes with short spaces therebetween may be used to illustrate an object, such as one underneath another, or to reference environment such as facial features; or for clarity, to show location, such as the space an object or structure will occupy, would occupy, or did occupy; or for illustrative purposes, to represent an object, structure, element or layer(s) as 'invisible' so that other objects more pertinent to the discussion at hand may be highlighted or more clearly seen.

A broken line including a long dash followed by a short space, a short dash and another short space is used to call out a centerline or an angle, or to indicate alignment; when accompanied by a bracket, to call out a section, segment or portion of an object or a group of objects; to illustrate a spatial relationship between one or more objects or groups of objects, or to create separation between objects for the purpose of illustrative clarity.

In the drawings accompanying this disclosure, like objects are generally referred to with common reference numerals or characters, except where variations of otherwise like objects must be distinguished from one another. Where there is a plurality of like objects in a single drawing figure corresponding to the same reference numeral or character, only a portion of said like objects may be identified. After initial description in the text, some reference characters may be placed in a subsequent drawing(s) in anticipation of a need to call repeated attention to the referenced object. Drawings are not rendered to scale, and where shown, the thickness of objects may be exaggerated for illustrative clarity.

BRIEF DESCRIPTION OF THE SEVERAL VIEWS OF THE DRAWING

FIG. 8 is a plan view of a third form of nasal dilator in accordance with the present invention.

FIG. 9 is a three-quarter perspective view of the nasal dilator of FIG. 8.

FIG. 10 is an exploded perspective view of the nasal dilator of FIG. 8.

FIG. 11 is a side elevation of a human face, depicted in broken lines, showing a perspective view of the nasal dilator of FIG. 8 engaged on the nose thereof.

FIG. 12 is a plan view of an alternate form of the nasal dilator of FIG. 8.

FIG. 29 is an exploded perspective view of the nasal dilator of FIG. 27.

FIG. 30 is a plan view of a seventh form of nasal dilator in accordance with the present invention.

FIG. 31 is a three-quarter perspective view of the nasal dilator of FIG. 30.

FIG. 32 is a perspective view of the resilient member structure of the nasal dilator of FIG. 30.

FIG. 37 is a plan view of an alternate form of the nasal dilator of FIG. 30.

FIG. 38 is a three-quarter perspective view of the nasal dilator of FIG. 37.

FIG. 39 is a plan view of an eighth form of nasal dilator in accordance with the present invention.

FIG. 40 is a three-quarter perspective view of the nasal dilator of FIG. 39.

FIG. 41 is an exploded perspective view of the nasal dilator of FIG. 39.

FIG. 42 is a plan view of an alternate form of the nasal dilator of FIG. 27.

FIG. 43 is a three-quarter perspective view of the nasal dilator of FIG. 42.

FIG. 44 is a plan view of an ninth form of nasal dilator in accordance with the present invention.

FIG. 45 is a three-quarter perspective view of the nasal dilator of FIG. 44.

FIG. 46 is a partially exploded perspective view of the nasal dilator of FIG. 44.

FIGS. 47, 50, and 53 are plan views of variations of a tenth form of nasal dilator in accordance with the present invention.

FIGS. 48, 51, and 54 are three-quarter perspective views of the nasal dilators of FIGS. 47, 50, and 53, respectively.

FIGS. 49, 52, and 55 are partially exploded perspective views of the nasal dilators of FIGS. 47, 50, and 53, respectively.

FIGS. 56, 59, and 61 are plan views of variations of an eleventh form of nasal dilator in accordance with the present invention.

FIG. 64 is a plan view of a twelfth form of nasal dilator in accordance with the present invention.

FIG. 65 is a three-quarter perspective view of the nasal dilator of FIG. 64.

FIG. 66 is an exploded perspective view of the nasal dilator of FIG. 64.

FIG. 67 is a side elevation of a human face, depicted in broken lines, showing a perspective view of the nasal dilator of FIG. 65 engaged on the nose thereof.

FIG. 68 is a plan view of an thirteenth form of nasal dilator in accordance with the present invention.

FIG. 69 is a three-quarter perspective view of the nasal dilator of FIG. 68.

FIG. 70 is an exploded perspective view of the nasal dilator of FIG. 68.

DETAILED DESCRIPTION OF THE INVENTION

Figure 3:
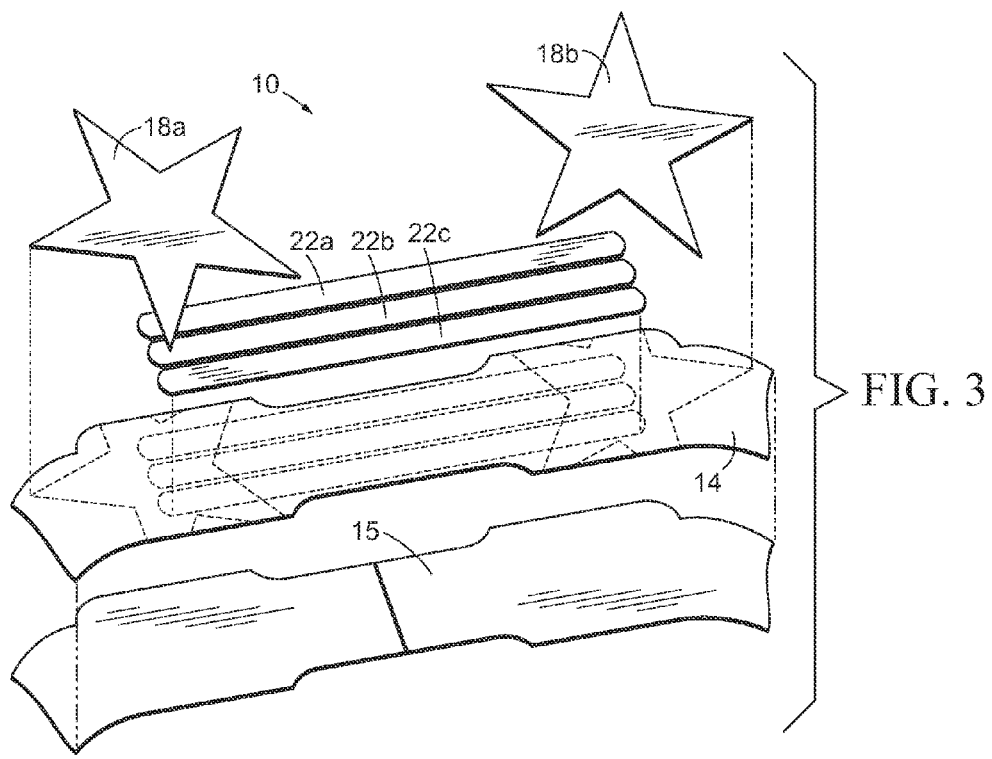
FIG. 3 is a three-quarter perspective view of the nasal dilator of FIG. 1.
Figure 2:
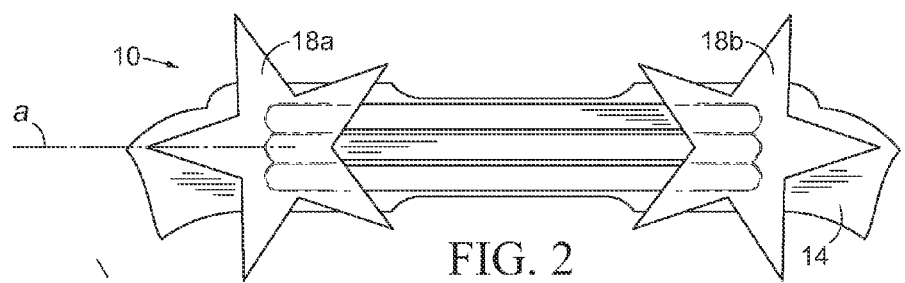
FIG. 2 is a plan view of the nasal dilator of FIG. 1.
Figure 1:
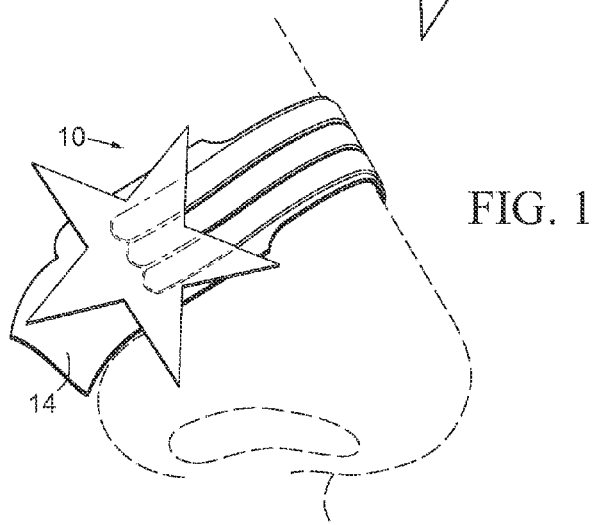
FIG. 1 is a perspective view showing a human nose, depicted in broken lines, with a perspective view of a first form of nasal dilator in accordance with the present invention engaged thereon.

An embodiment of a nasal dilator, 10, in accordance with the present invention, is illustrated in FIG. 1. Dilator 10 is engaged to and flexed across a human nose, represented by dashed lines, and secured to the nose on each side of the bridge thereof. As seen in FIG. 3, the dilator may be comprised of layers of several thin sheets, including a base layer, a resilient layer and a cover layer. The dilator engagement element may be primarily comprised of the base layer and/or a cover layer, including at least one base member, 14 (if a plurality thereof, 14*a*, 14*b*, etc.), and/or at least one cover member, 18, (if a plurality thereof, 18*a*, 18*b*, etc.). The layers of dilator 10 may be substantially aligned along a longitudinal centerline, a, as seen in FIG. 2.

The preferred material for the dilator base and cover layers is from a group of widely available flexible, supple nonwoven fabrics that are breathable and comfortable on the skin, as may be found, for example, among the class of convertible medical grade adhesive tapes. Certain flexible, supple thermoplastic films, as also may be found among the class of medical grade tapes, as well as colored or clear films, are equally preferred. A pressure sensitive adhesive, preferably biocompatible with human skin, may be disposed on at least one flat surface side of the preferred material, which may, in turn, be covered by a removable protective release liner.

The dilator resilient element comprises a resilient member structure including at least one resilient member, 22, (if a plurality thereof, 22*a*, 22*b*, and 22*c*, etc.) in at least one resilient layer. The preferred material for the resilient element is a thermoplastic resin. The preferred material may be selected from a class having a range of flexural, tensile and elastic moduli so as to have substantial in-plane rigidity and out-of-plane flexibility, such that resilient member 22 has suitable spring biasing properties at a thickness, for example, of from about 0.005" to about 0.015". The most preferred thermoplastic material from said class is a widely available biaxially oriented polyester resin (PET or boPET). Softer thermoplastics, such as those that may be extruded or thermoformed, for example, may be preferable in instances where a thicker (i.e., >0.015"), or more three dimensional, resilient member or structure is desired.

Preferred resilient element materials may have a pressure sensitive adhesive disposed on at least one surface, which may be covered by a removable protective release liner. The material may be laminated to the preferred base layer or cover layer material so that one or more resilient members and at base or cover members may be die cut concurrently to the same peripheral shape.

As further seen in FIG. 3, a protective layer of release liner, 15, may be used to cover any exposed adhesive preliminary to using the dilator. The shape and dimensions of release liner 15 may correspond to the periphery of dilator 10 or may exceed the periphery of one or more dilators 10. Release liner 15 may be bisected into two parts, which may overlap or abut, so as to facilitate removal from the dilator prior to use.

Figure 4:
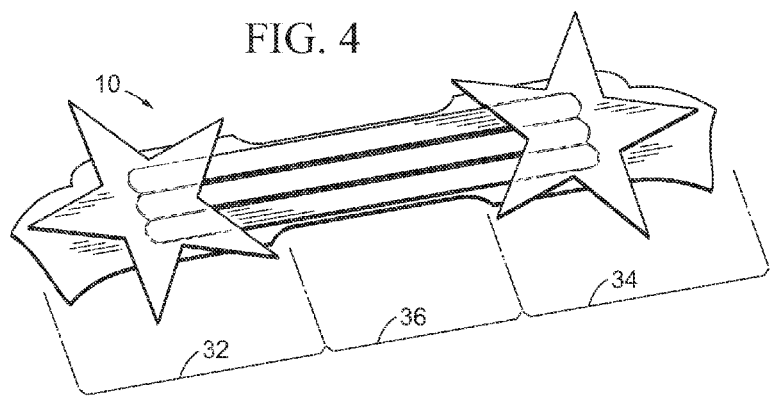
FIGS. 4 and 5 are exploded perspective views, respectively, of the nasal dilator of FIG. 1.
Figure 5:
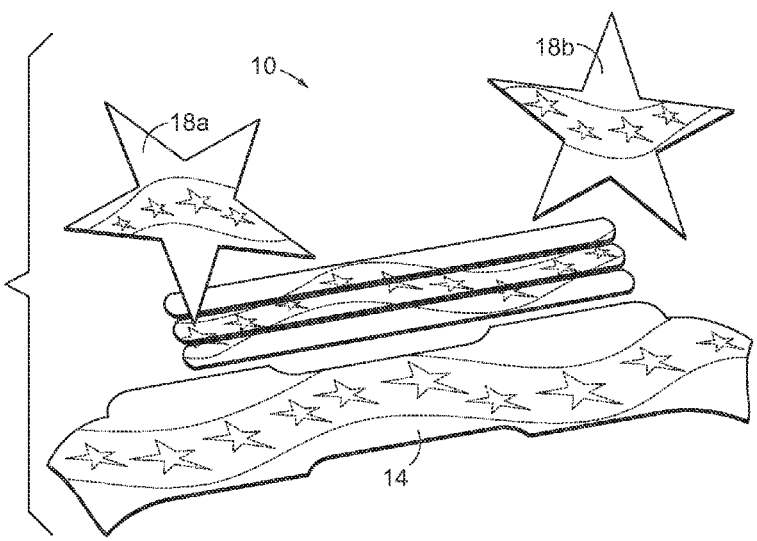

FIG. 4 illustrates that the individual layers of dilator 10 may be combined into a laminate, the laminate forming a unitary, or single body, truss. The dilator has contiguous regions indicated generally by broken lines and brackets, including a first end region, 32, a second end region, 34, and an intermediate region, 36, which interconnects first end region 32 to second end region 34. The width of intermediate region 36 may be narrower, equal to, or wider than the width of end region 32 or 34. Portions of any layer may define a region of the dilator or a portion thereof. The elements, layers, or members of dilator 10 may extend from one region to another. End regions 32 and 34 are identical in peripheral configuration and in size and shape. That is, they are the mirror images of each other. However, in rendering a desired decorative design element, the end regions may be configured asymmetric or non-identical to each other, as seen, for example, in FIGS. 6-7.

FIGS. 1-5 further illustrate a decorative design element formed by a combination of the base, resilient and cover layers of dilator 10, their peripheral boundaries, and surface areas defined by the peripheral boundaries: the base member may be interpreted as being in the shape of a banner; the resilient layer, or resilient member structure, may be interpreted as horizontal stripes; and the cover layer includes two spaced apart star-shaped members. To enhance the design element, each of the members may be in a color, such as, for example, red, white or blue. To further enhance the design element, each member may be imprinted with a design, represented by dashed lines, as shown, for example, in FIG. 5. The imprinted design may include the same or additional colors.

Each member of each layer may contribute a portion of the decorative design element; the combined layers and members thus form the decorative design element as a whole. For example, the base layer ("banner") contributes to device function by providing the primary engagement element by which the dilator is secured to the nose, as particularly seen in FIG. 4. The resilient member structure ("stripes") contributes to device function in that it provides the resilient means, or resiliency, of the dilator, as discussed hereinbefore. The cover members ("stars") may be configured to secure the end portions of the resilient members to the base layer.

The decorative design element, or shaped design, may be configured, in part, without regard to the most efficient shape that could be used if dilator 10 were undecorated. For example, star shapes are not the most efficient shape for a nasal dilator cover member(s), but they nonetheless serve both device function as well as decorative function. One of ordinary skill in the art may observe that a conventional rectangular nasal dilator resilient member lends itself to the 'stripes' portion of the decorative design element depicted in the embodiment of FIGS. 1-5. However, other embodiments of the present invention illustrate that a resilient member structure may be shaped to render all or part of a shaped design as well as function with suitable resiliency.

Dilator layers may be stacked in any order. For example, the base and cover layers may be interchanged, or the base and/or cover layers may be eliminated in whole or in part, or the cover layer may be interposed between the resilient layer and the skin surfaces engaged by the dilator. Any or all of resilient members 22*a*, 22*b* and 22*c* may alternatively be uppermost in the stacking order of the dilator layers. The cover layer is divided into two parts, or members, each member defining at least a portion of each end region of the dilator. Alternatively, the base and cover layers of the dilator may be fabricated concurrently so as to have the same peripheral shape, or the base and resilient layers may be fabricated concurrently to the same peripheral shape, or the base layer may have a greater surface than the resilient layer(s) but lesser than the cover layer.

Where the base layer has a significantly lesser surface area than the cover layer, adhesive on the skin-engaging side of the base layer may be optionally eliminated in whole or part, creating an adhesive void thereat. With or without adhesive, the base layer may also serve as a compressible buffer between the device and the skin, as has been historically common in medical devices that remain in contact with the skin for any length of time.

Figure 6:
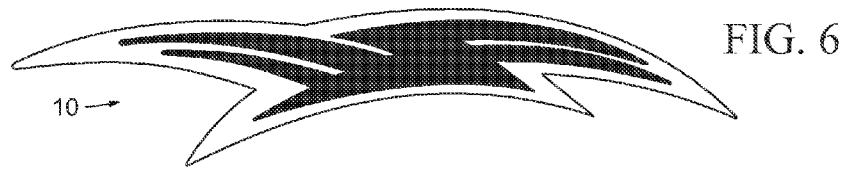
FIG. 6 is a plan view of a second form of nasal dilator in accordance with the present invention.
Figure 7:
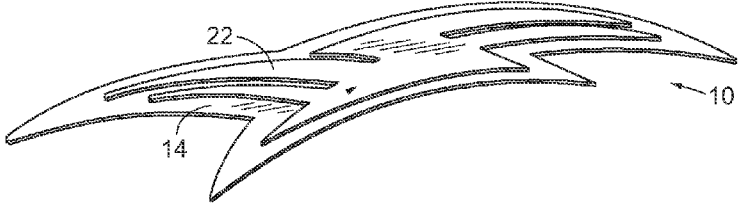
FIG. 7 is a three-quarter perspective view of the nasal dilator of FIG. 6.

FIGS. 6-14 illustrate embodiments in accordance with the present invention wherein the layers of dilator 10 are peripherally shaped to complement each other to form the decorative design element. In FIGS. 6 and 7, resilient member 22 includes spring finger components extending outwardly from a common center. In FIGS. 8-11, a single resilient member has a plurality of openings shaped to artistically complement the resilient member peripheral outline. The dilator of FIG. 6 has an asymmetric peripheral shape, while the dilator of FIG. 8 is symmetric on both sides of its lateral centerline, b. In either instance, however, resilient member 22 is preferably configured to have similar resiliency, or spring biasing force, at both end regions of the dilator.

An example of a directional element may be seen in the resilient members shown in FIGS. 6 and 8. Both are both shaped wider at a mid-portion thereof and narrower at each end portion, transitioning more or less gradiently from one to the other. The directional element thus gradiently reduces resiliency at the dilator end regions.

In FIGS. 6 and 8, the engagement element is shaped to complement the shaped design formed by the resilient member periphery. In FIG. 6, base member 14, though asymmetric, is configured to have substantially similar engagement surface area at each end region of the dilator. In FIG. 8, the base layer comprises two, or alternatively, three members (14*a*, 14*b* and 14*c*). The latter is particularly illustrated in FIGS. 8, 9 and 11, whereas FIG. 10 shows base member 14*c* depicted in dashed lines to indicate that it may be optionally eliminated. A portion of resilient member 22 is also depicted in dashed lines to illustrate its position when secured to the base layer.

Figure 13:
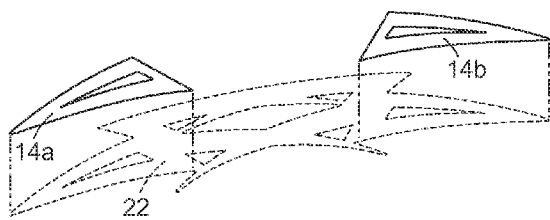
FIG. 13 is an exploded perspective view of the nasal dilator of FIG. 12.
Figure 14:
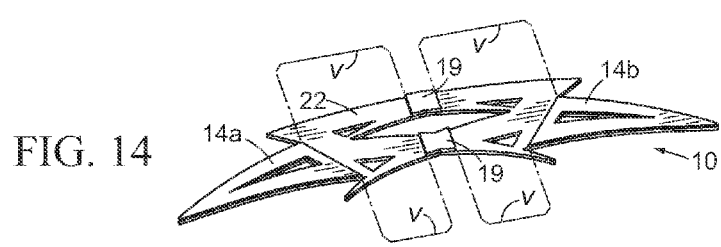
FIG. 14 is a three-quarter perspective view of the nasal dilator of FIG. 12.
Figure 15:
FIG. 15 is a plan view of an alternate form of the nasal dilator of FIG. 6.
Figure 16:
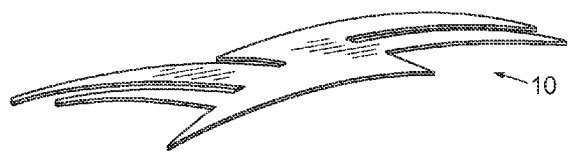
FIG. 16 is a three-quarter perspective view of the nasal dilator of FIG. 15.

FIGS. 12-16 illustrate embodiments of the present invention wherein a resilient member structure may form the dilator at least substantially in its entirety. To configure dilator 10 to function as desired, resilient member 22 includes a directional element in the form of openings within its periphery, and/or a lesser width at the end portions compared to the mid-portion, that gradiently reduces spring biasing forces at the end regions. The dilator of FIGS. 12-14 is symmetric about its lateral centerline, while the dilator of FIGS. 15-16 is asymmetric thereby.

As further seen in FIG. 14, dilator 10 may include discreet spaced apart base members 14*a* and 14*b*, secured to each end region, as seen, for example, in FIG. 14. For illustrative clarity, FIGS. 13 and 14 depict the underside, or skin-facing side, of the dilator. Dilator 10 may also include one or more of a centrally located absorbent pad, 19, secured to the underside, or skin-facing side, thereof. The pads prevent the dilator from contacting the skin at the bridge of the nose thereat. A contact void, v, adjacent thereto, extends approximately between the edges of pad 38 to the each edge of base members 14 at the dilator end regions. Like an adhesive void, contact void v allows less contact with the skin compared to a base layer with a continuous adhesive disposed on its skin-engaging side. Contact void v generally contributes to user comfort, and dilator 10 may be more easily removed from the skin surface with less stress thereto. Pad 19 may include an adhesive disposed on its skin-engaging surface, or not, as may be preferred.

Figure 17:
FIG. 17 is a plan view of a fourth form of nasal dilator in accordance with the present invention.
Figure 18:
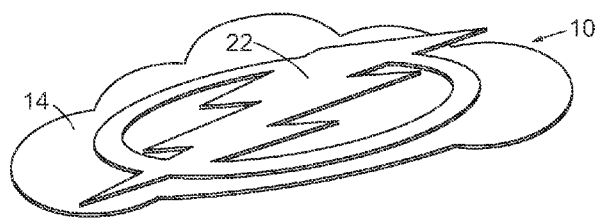
FIG. 18 is a three-quarter perspective view of the nasal dilator of FIG. 17.
Figure 20:
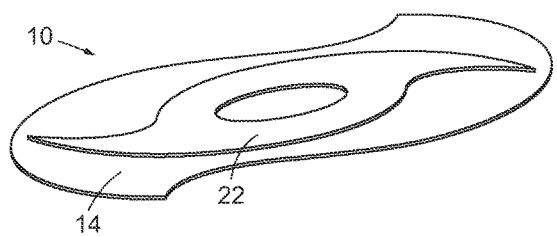
FIG. 20 is a three-quarter perspective view of the nasal dilator of FIG. 19.
Figure 19:
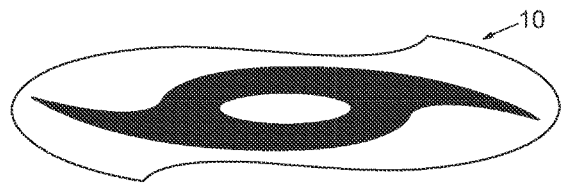
FIG. 19 is a plan view of an alternate form of the nasal dilator of FIG. 17.
Figure 22:
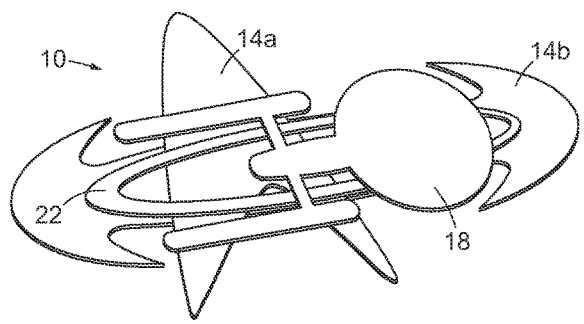
FIG. 22 is a three-quarter perspective view of the nasal dilator of FIG. 21.
Figure 21:
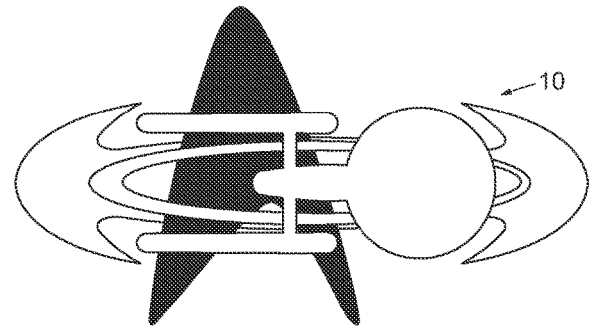
FIG. 21 is a plan view of a fifth form of nasal dilator in accordance with the present invention.
Figure 23:
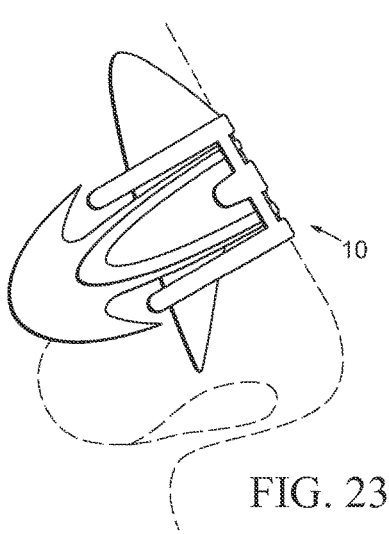
FIGS. 23 and 24 are side elevations of a human face, depicted in broken lines, showing perspective views, respectively, of the nasal dilator of FIG. 21 engaged on the nose thereof.

FIGS. 17-32 illustrate embodiments of the present invention wherein the resilient and engagement elements are disparately shaped, but artistically complementary. The embodiments also correspond to, or otherwise evoke, imagery or whimsy that may be generally recognizable. For example: 'clouds and lightning' as seen in FIG. 17; an interpretation of the National Weather Service symbol for a tropical storm or hurricane as seen in FIG. 19; a 'spacecraft' in FIG. 21; and 'superheroes' as seen in FIGS. 25-32.

FIGS. 21-24 further illustrate that multiple dilator layers may each contribute to the decorative design element. For example, cover layer 18 may be seen as a top-down plan view of an 'interstellar spacecraft'; resilient member 22 and base member 14*b* may be seen as representing a 'warp field' generated by the craft; and base layer 14*a* may be seen as a symbol of an 'interstellar cooperative body' to which the craft belongs. The layers of the dilator seen in FIGS. 21-24 may also be described in terms of their function and stacking order. For example: a shape corresponding to a spacecraft may function as the resilient layer or the cover layer; a shape(s) corresponding to a warp field may function as an engagement layer or resilient layer; and a shape corresponding to an interstellar body may be determined to function as an engagement layer or, alternatively, as a purely decorative layer.

Combining a geometric shape, such as an ellipse or rhombus to the resilient member structure can help evenly distribute its spring constant, particularly as seen, for example, in FIGS. 25, 27, 39, and 44-47. The combination is useful when, for example, it is desired that resilient member 22 form the decorative design element, but where the desired design is irregularly shaped, or cannot be rendered generally oblong, or does not have a length somewhat greater than its width. The combination of a shaped design and geometric shape may be coextensive, and thus fabricated from the same material, as seen, for example, in FIGS. 25-26, 30-38, and 68-70. Alternatively, the combination may overlap or be overlaid, as seen, for example, in FIGS. 21-24, 27-29, 39-55, and 64-67.

A shaped design may be positioned substantially at the dilator intermediate region when combined with a geometric shape. The dimensions of upper and lower horizontal portions, p, of the geometric shape substantially determine the extent of resiliency it contributes to the resilient member structure, as seen, for example, in FIGS. 25-26, 34, 38 and 66. The dimensions of p must be taken into consideration when configuring the resilient member structure and its spring biasing properties.

Figure 26:
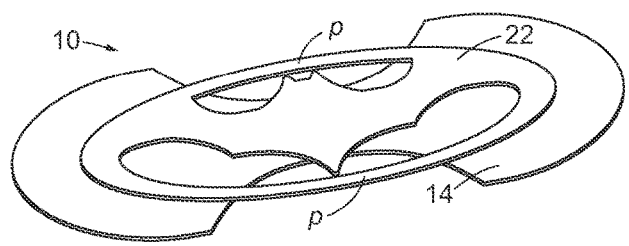
FIG. 26 is a three-quarter perspective view of the nasal dilator of FIG. 25.
Figure 25:
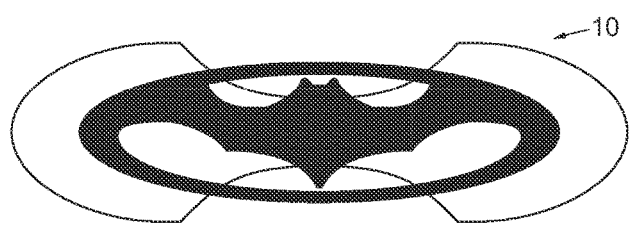
FIG. 25 is a plan view of an alternate form of the nasal dilator of FIG. 17.
Figure 24:
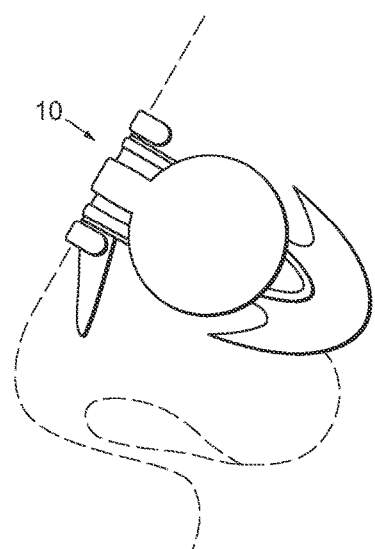

FIGS. 25 and 26 illustrate an example of a resilient member structure that combines an ellipse coextensively with a shaped design. The shaped design is contained substantially within the periphery of the ellipse, oriented generally horizontally between its opposite ends. The ellipse is preferably configured to artistically complement the shaped design as well as complement the resiliency that will result from the shaped design's overall dimensions. In this case, the ellipse is substantially symmetric about its lateral and longitudinal centerlines, and gives the resilient member structure a length to width ratio conducive to rendering suitable spring biasing force. Overall, resilient member 22 has slightly greater surface area at its mid-portion, and slightly less surface area at its ends, resulting in a roughly gradiently tapered overall width/surface area that generally results in gradiently reduced resiliency at each end region of dilator 10.

Nasal dilator devices of the present invention may include resilient member structure comprising two or more resilient members arranged in a spatial relationship, such as adjacent, or overlapping or overlaid one atop another. For example, a shaped design may be combined with one or more generally oblong or somewhat rectangular resilient members, as seen, for example, in FIGS. 27-29 and 42-55.

Figure 28:
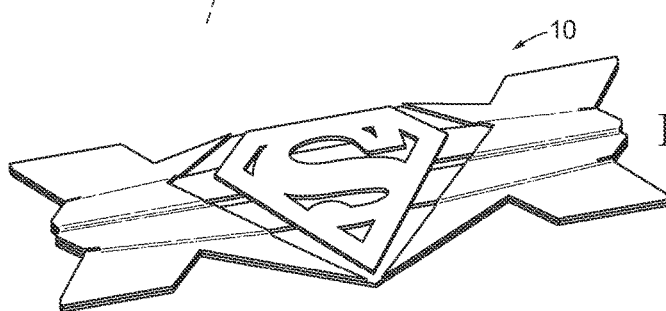
FIG. 28 is a three-quarter perspective view of the nasal dilator of FIG. 27.
Figure 27:
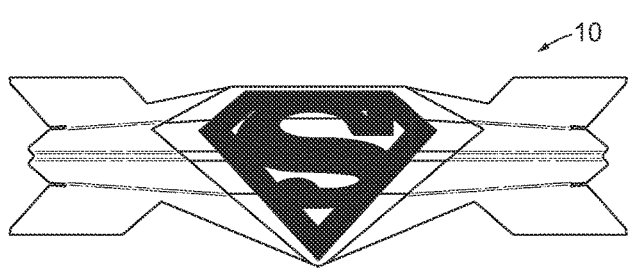
FIG. 27 is a plan view of a sixth form of nasal dilator in accordance with the present invention.

In FIGS. 27-29 a shaped design and a geometric diamond are combined into resilient member 22c. In FIGS. 42-43 several interconnected shapes (symbols, characters, or the like) extend across at least the intermediate region of dilator 10. In both instances, resilient member 22c overlaps a pair of elongated, generally rectangular resilient members 22a and 22b, which extend from one dilator end region to the opposite end region. Resilient members 22a and 22b are generally oblong, and as seen in FIGS. 27-29, are slightly wider in the middle and narrower at each end, their peripheral outlines being somewhat angular so as to artistically complement the angular lines seen in the other layers of dilator 10.

FIGS. 27-29 further illustrate two shaped cover members 18a and 18b, their peripheral outlines corresponding to the dilator end region outer edges while the inside edges frame resilient member 22c. Base member 14 defines the overall periphery of dilator 10, but could be configured match the periphery of the resilient members, or be configured to have lesser surface area than the base member, or a greater surface area than any of the resilient members.

Where a shaped design is centrally located in the intermediate region of dilator 10, the spring constant of the resilient member structure may be significantly lesser at the dilator end regions. Accordingly, resilient member 22c may be of a thinner or softer preferred material so that when combined with resilient members 22a and 22b, the dilator's spring constant is more evenly distributed along the length of dilator 10. Alternatively, resilient member 22c may be configured by material type or thickness to contribute more or less resiliency to the resilient member structure. For example, a preferred resilient element material having a higher flexural, tensile or elastic modulus may be correspondingly thinner. A thicker material, which would render a more three-dimensional shaped design, may preferably have comparatively lesser flexural, tensile or elastic modulus values. (FIG. 27 illustrates an example of the former, FIG. 64 illustrates an example of the latter.) Alternatively, resilient member 22c could be configured as primarily, substantially, or purely decorative.

A shaped design in a resilient member structure may include spring finger components, 23, extending outward to each end region of dilator 10, terminating at or near the end edges thereof, as seen, for example, in FIGS. 30-38. In these instances, the resilient member structure is a single, coextensive unit, rather than one resilient member overlaid onto another.

Spring finger components 23 may be any shape or configuration; they may be straight or curve, or have a constant or tapered width. They may be of any length or width, but are preferably substantially uniform or otherwise consistent with the dilator's design element. Spring fingers 23 may be separated by a slot or elongated opening, which defines lateral spacing, or distance, between the spring finger inside long edges. The spaced apart spring fingers also allow greater axial torsional flexibility so that dilator 10 may more closely conform to the skin surface of the nose.

As particularly seen in FIG. 31, spring fingers 23 may terminate inboard of the end edges of dilator 10 such that engagement material extends around the spring finger terminal ends for securing dilator end regions to the skin surface of the nose. (Alternatively, resilient member terminal ends may extend to, and conform with, the dilator's end edges, as seen, for example, in FIGS. 27-29 and 33-60.)

Resilient member terminal ends may also conform with corresponding scalloped dilator end edges that form a horizontal protrusion thereat. When the dilator is flexed across the nose, the horizontal protrusion separates slightly from the skin and changes the angle of spring biasing forces, shifting a portion of spring biasing forces from primarily peel forces to primarily shear forces. Shear forces are more easily withstood by the adhesives typically used to adhere medical devices to human skin, thus adhesive engagement to the nasal outer wall tissues may be improved as a result.

Spring fingers 23 may be aligned so as to generally correspond with horizontal portions of a shaped design. For example, FIG. 32 separates the resilient member along imaginary dashed lines that correspond to the shaped design horizontal portions. The resilient member structure may thus be figuratively viewed as three laterally adjacent, parallel, generally oblong resilient members. Each member is wider at its mid-portion, having more surface area thereat, than at its terminal ends.

FIG. 37 illustrates another example of aligning spring fingers with horizontal portions of a centrally located shaped design. Spring fingers 23 extend approximately from the horizontal portions p of the shaped design. Additionally, spring fingers 23 are angled so their ends terminate substantially equidistant from longitudinal centerline a. Artistically, the angled fingers form part of the decorative design element.

Figure 34:
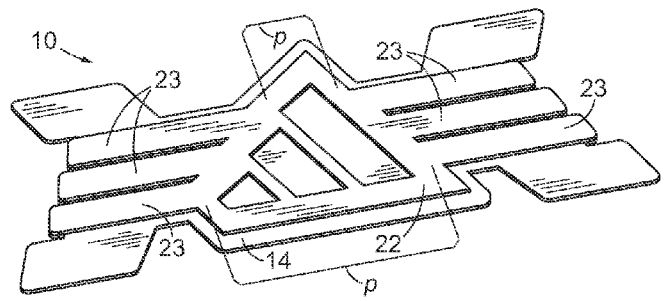
FIG. 34 is a three-quarter perspective view of the nasal dilator of FIG. 33.
Figure 33:
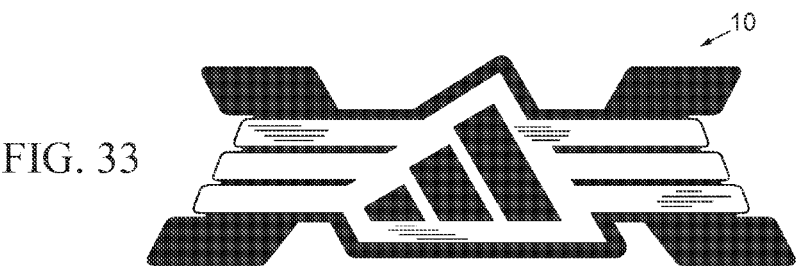
FIG. 33 is a plan view of an alternate form of the nasal dilator of FIG. 30.
Figure 36:
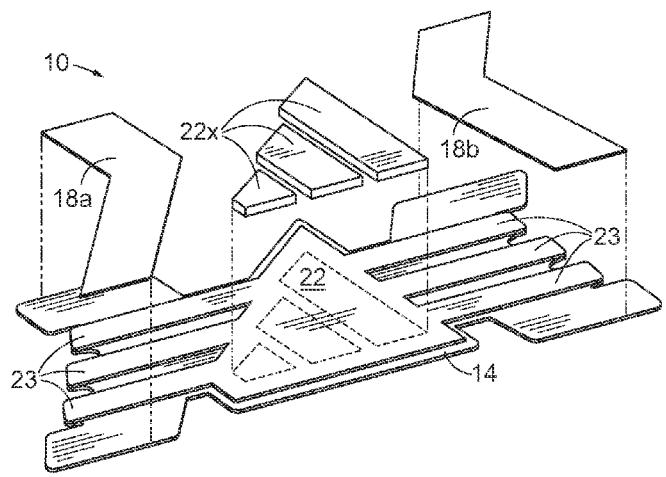
FIG. 36 is a partially exploded perspective view of the nasal dilator of FIG. 35.
Figure 35:
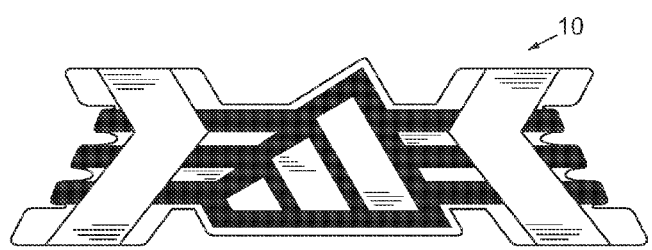
FIG. 35 is a plan view of an alternate form of the nasal dilator of FIG. 33.

The embodiments of FIGS. 33-36 also include coextensive spring fingers 23 extending outward from a centrally positioned shaped design. FIGS. 33-34 illustrates that a portion of the shaped design may be formed by similarly shaped openings within its periphery, rendering three staggered shapes. Alternatively, FIGS. 35-36 illustrate that those same shapes, 22x, may be overlaid onto resilient member 22. FIG. 35 further illustrates the addition of cover members 18a and 18b shaped to artistically complement the design element.

FIGS. 39-41 illustrate a plurality of spring finger components 23 that are an integral part of the dilator's design element yet are entirely functional. The fingers fan out laterally, corresponding and conforming with similarly shaped base member 14 and shaped cover members 18a and 18b. The effect may be artistically viewed as a pair of wings with feathers emanating outward. The design element further includes a shaped design symbol as resilient member 22b. As discussed hereinbefore, since portions p of resilient member 22b are relatively slight, it may be formed more or less rigid or thick, or more or less decorative or functional, as may be desired.

A design element may also include a plurality of symbols, shapes, characters, or the like, overlaid onto and extending along some, most, or all of the length of one or more generally oblong or rectangular resilient members, as seen, for example, in FIGS. 42-52.

A plurality of symbols may be joined together coextensively to form a shaped design, as seen, for example, in resilient member 22c of FIG. 43. The shaped design is overlaid onto a pair of spaced apart, substantially rectangular resilient members 22a and 22b. In the present instance, however, resilient member 22c forms substantially all of the decorative design element.

In FIGS. 44-52, a plurality of design shapes 22x (symbols, characters, or the like) are spaced apart along at least one oblong resilient member. As seen in FIG. 46, each shape is secured to a pair of spaced apart parallel resilient members, the shapes spanning the lateral distance between, and aligning with, outer long edges of the resilient members. An additional shaped design, depicted as resilient member 22c (but which could alternatively be a base member), artistically complements the design element. Additionally, the engagement corner tabs, 35, of the base layer are shaped, or configured, to artistically complement the design element. It will be apparent to one of ordinary skill in the art that absent their design elements, the dilators of FIGS. 43 and 45 could otherwise be viewed as a substantially conventional two-band nasal dilator.

FIGS. 47-55 illustrate examples of a design element incorporated into nasal dilator resilient member structures having three resilient members, or three resilient members having end portions that diverge to discreet engagement contact points, or two resilient members, respectively. In each case the design element includes a plurality of discreet shaped designs (symbols, characters, or the like), either overlaid onto, or coextensive with, at least one resilient member. An additional resilient member 22d may be in the form of a geometric shape, as discussed hereinbefore, as part of the resilient member structure. Base member 14 is configured to further artistically complement the design element.

The dilator of FIGS. 47-49 includes three rectangular, spaced apart, substantially parallel resilient members 22a, 22b and 22c. A bonding member, 16, as seen, for example, in FIG. 49, may be positioned between any two layers or members of dilator 10 to secure them together and/or space them apart vertically. Bonding member 16 may comprise an adhesive substance, a carrier material, or a carrier material with an adhesive substance disposed on one or both flat surface sides whereby to bond two dilator layers or members together. In this case, bonding member 16 secures at least some of shapes 22x to resilient member 22c. Some shapes 22x may be secured to rhombus-shaped resilient member 22d.

Figure 52:
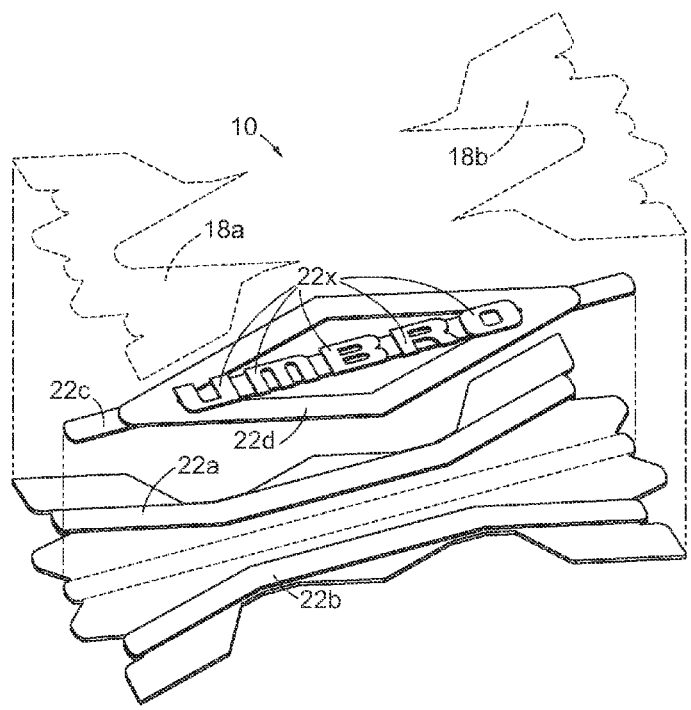
Figure 51:
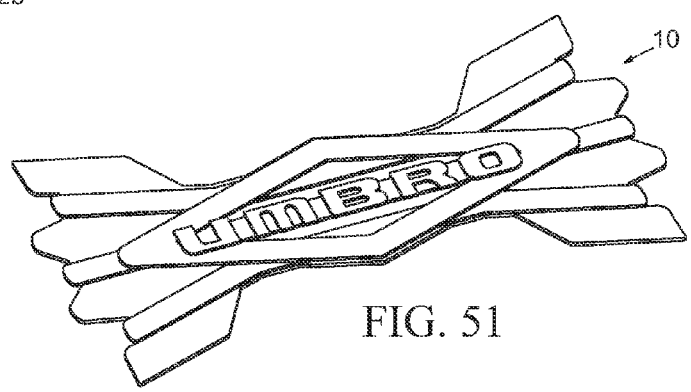
Figure 50:
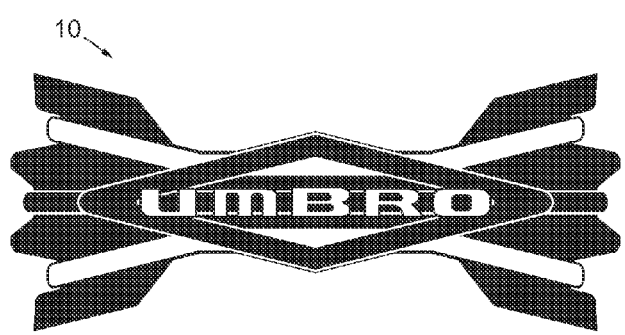

The dilator of FIGS. 50-52 includes resilient member 22a extending substantially along the longitudinal centerline thereof, plus resilient members 22b and 22c laterally adjacent to each side thereof. Resilient members 22b and 22c have divergent end portions that artistically complement a rhombus shape, which in turn frames a plurality of symbols or characters. The divergent end portions also laterally spread spring biasing forces of dilator 10 to a greater lateral extent than, for example, the dilator of FIG. 47 or 53. The resilient members terminate at three discreet engagement contact points spaced apart along the lateral ends of the dilator. FIG. 52 further illustrates, by dashed lines, optional cover members 18a and 18b, shaped to artistically complement the centrally located rhombus shape. The cover members correspond to the outer edges of each end region of the dilator, the outer edges themselves shaped to artistically complement the decorative design element.

The decorative design element of the dilator of FIGS. 53-55 includes a plurality of shaped symbols or characters that extend coextensively between a pair of spaced apart, substantially parallel, oblong resilient members. The characters interconnect the two spaced apart resilient members along their respective inside long edges so as to form a single coextensive unit, resilient member, 22a.

FIG. 55 further illustrates resilient members 22b and 22c positioned along the long edges of resilient member 22a. Resilient members 22b and 22c are meant to more clearly define the plurality of shapes extending along resilient member 22a, by effectively providing a sharp long edge that allows the characters to more clearly stand out (as more clearly seen in FIG. 53). Resilient members 22b and 22c may be more functional or less functional (i.e., having greater or lesser resiliency), depending upon the degree of resiliency configured into resilient member 22a. Alternatively, resilient members 22b and 22c could be configured instead as primarily decorative, or further alternatively, as bonding members (16), as described with regard to FIG. 49.

The dilator of FIGS. 56-59 illustrate a design element formed by adjacent long edges of two spaced apart resilient members. A portion of the shaped design is defined by each long edge of the adjacent resilient members, such that the space between the adjacent resilient members substantially forms the interior thereof. That space is a portion of the surface area of the engagement element underneath the adjacent resilient members, which is preferably in a contrasting color so as to highlight the decorative design element, as particularly illustrated in FIG. 56.

Figure 57:
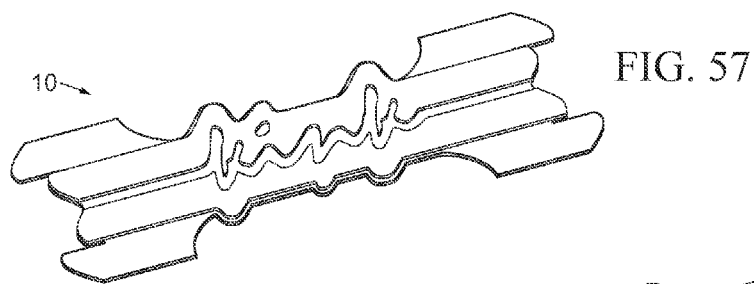
FIGS. 57, 60, and 62 are three-quarter perspective views of the nasal dilators of FIGS. 56, 59, and 61, respectively.
Figure 58:
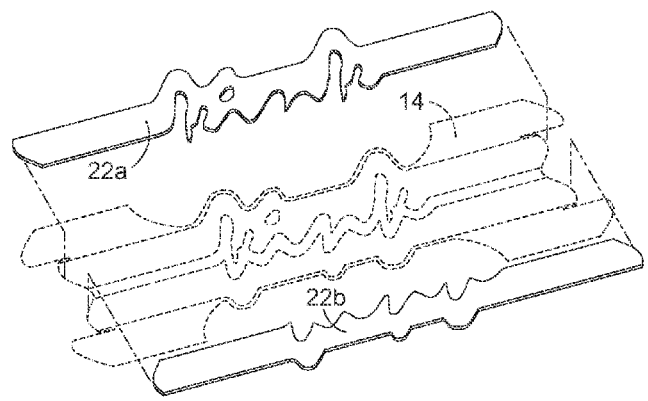
FIGS. 58 and 63 are partially exploded perspective views of the nasal dilators of FIGS. 56 and 61, respectively.

For illustrative clarity, FIG. 58 shows resilient members 20a and 20b spaced apart as well as proximate each other as seen in FIGS. 56 and 57. The two facing inside edges, combined, form the periphery of the shaped design—in the present example, a plurality of interconnected symbols or characters. FIG. 58 further illustrates that the shaping of the resilient members' inside long edges may extend inward in part, effectively narrowing the resilient member width/surface area thereat. To maintain a consistency of width, as well as more artistically frame the shaped design, the opposite, outer, long edge may also be similarly shaped, but extending outward, so as to be roughly consistent with those portions of the inside long edge extending inward.

Figure 59:
Figure 60:
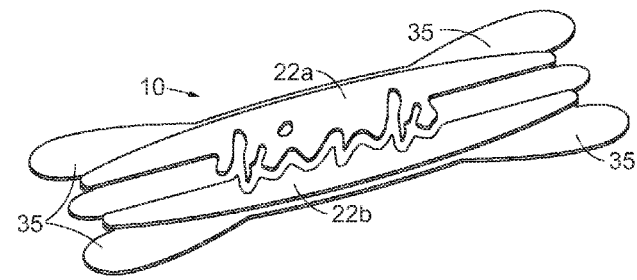

Alternatively, FIGS. 59-60 show the resilient member outside long edges curved arcuately, which creates greater width along the resilient members' mid-portions—in lieu of shaping the outside long edges as just described. Additionally, the curve allows for a gradient decrease in width/surface area, and thus gradiently reduced resiliency at the dilator end regions, as discussed hereinbefore. Artistically, the arcuate shape visually frames the shaped design formed by the resilient members' inside long edges. Corner tabs 35 of dilator 10 are also shaped to artistically complement the arcuate shape of the resilient member structure.

Figure 63:
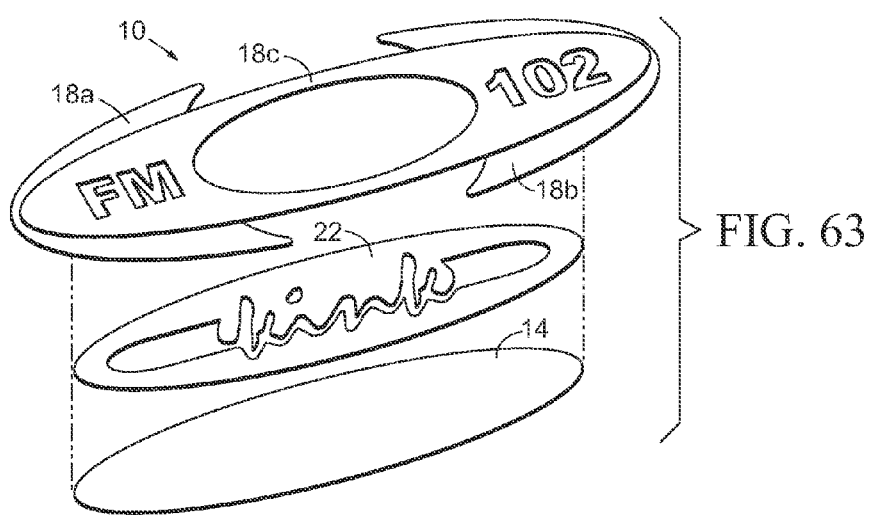
Figure 62:
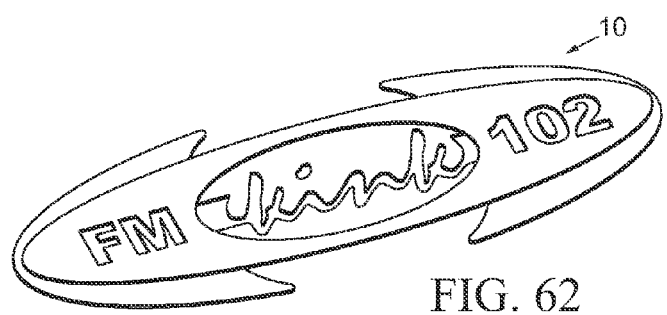
Figure 61:

The dilator of FIGS. 61-63 shows that resilient members 22a and 22b, as seen in FIG. 60, may be interconnected at or near their terminal ends so as to form a single coextensive structure having an elliptical periphery with a shaped design formed within the periphery. FIG. 63 illustrates base member 14 having substantially the same peripheral shape as resilient member 22. Discreet cover members 18a and 18b are also shaped to artistically complement the shape of resilient member 22. An additional cover member 18c includes an ellipse and a shaped design formed within its elliptical periphery, the ellipse artistically framing the shaped design of resilient member 22. Cover member 18c could optionally, or alternatively, be configured as an additional resilient member.

The design elements of dilators 10 as seen in FIGS. 64-67 are configured around a plurality of artistically complementary ellipses and/or curved lines. All of the layers of dilator 10 contribute to the design element, as described hereinbefore. Base member 14 defines a general periphery of dilator 10, and discreet cover members 18a and 18b match the end portions of base member 14 and artistically frame the outside edges of resilient member 22b, a complete shaped design by itself. As particularly seen in FIG. 66, resilient member 22a is shaped as an ellipse, but may alternatively be any suitable oblong shape. Resilient member 22b is interposed horizontally between cover members 18a and 18b.

As discussed hereinbefore, a shaped design may be fabricated from a softer, thicker material so as to accentuate a three-dimensional appearance. Horizontal portions p of resilient member 22b are relatively narrow, so greater thickness or rigidity, as discussed hereinbefore, may be preferable.

FIGS. 68-70 illustrate a plurality of interconnected, but coextensive complementary ellipses that together form a shaped design resilient member structure. The peripheral shape of base member 14 corresponds to the periphery of resilient member 22. Alternatively, the resilient member structure could be formed by a plurality of individual ellipses overlaid or overlapping onto one another. (Similarly, a combination of ellipses could be coextensive, with one or more additional ellipses overlaid thereon.) Discreet cover members 18 are configured to enhance the ellipses at the center of the shaped design, as particularly seen in FIG. 68.

It is appreciated that in many embodiments of the present invention, the design element contributes to or affects the resilient spring force of the dilator. Thus, one useful way of distinguishing an inventive article from the prior art is to consider the resilient force of the dilator in question, compared to a dilator without the decorative design element. In many embodiments, the two dilators will have different spring forces. That is, removing the design element alters the spring force. A non-functional and purely decorative design, such as a printed design, would not materially alter the spring force of the printed dilator compared to an unadorned dilator.

The foregoing descriptions and illustrations are intended to reveal the scope and spirit of the present invention and should not be interpreted as limiting, but rather as illustrative of the inventive concepts and techniques thereof. Insubstantial changes, modifications and alterations of the present disclosure are intended to be fully covered hereby.

I claim:

1. A nasal dilator, comprising a resilient element comprising: a resilient comprising first and second resilient members; and an engagement element, wherein a portion of at least one peripheral edge of the second resilient member and a corresponding surface area of the engagement element adjacent said at least one peripheral edge form at least a portion of a predetermined artistic design, such that a decorative design element is integrated into the second resilient member and the engagement element, and wherein a resilient spring force of the nasal dilator is different from a resilient spring force of a similar dilator from which the decorative design element is omitted, and wherein at least a portion of the decorative design element corresponds to all or part of a character, letter, symbol, title, crest, logo, geometric shape, emblem, mark, indicia, graphic decoration, representation, acronym, word, phrase, message, or expression.

2. The nasal dilator as in claim 1, wherein the decorative design element is configured to identify, represent, be associated with, or correspond to at least one of a team, program, sport, organization, sponsor, institution, club, school, company, product brand, service brand, corporate brand, legal entity, or individual.

3. The nasal dilator as in claim 1, wherein:
the resilient element comprises at least one resilient member;
the engagement element comprises at least one of a base member or cover member, or comprises at least one of a base member and a cover member; and
the at least a portion of a predetermined artistic design is formed in the at least one resilient member, and further formed in at least one base member or cover member.

4. The nasal dilator as in claim 1 wherein:
the resilient element comprises a resilient member structure including at least one resilient member;
the engagement element comprises an adhesive layer secured to at least a portion of a surface side of the resilient member structure;
the at least a portion of a predetermined artistic design is formed substantially in the resilient member structure; and
the resilient member structure at least defines the outer periphery of the dilator and overall appearance of the decorative design element.

5. The nasal dilator as in claim 1, formed as a laminate of thin sheets, the sheets vertically stacked by layers, the layers corresponding to the resilient and engagement elements, each layer comprising at least one member; the layers and members selected from the group consisting of:
a) a base layer having at least one undecorated base member;
b) a resilient layer having at least one undecorated resilient member;
c) a cover layer having at least one undecorated cover member;
d) a decorative layer, configured as primarily, or purely decorative, the decorative design element formed, at least in part, therein;
e) a base layer having at least one base member, the decorative design element formed, at least in part, therein;
f) a resilient layer having at least one resilient member, the decorative design element formed, at least in part, therein; or
g) a cover layer having at least one cover member, the decorative design element formed, at least in part, therein.

6. The nasal dilator as in claim 1, further comprising at least one of an interior opening, wherein:
at least one said peripheral edge is inboard from an outer peripheral edge of the at least one of the resilient and engagement elements, separated therefrom by said corresponding surface area; and
the inboard peripheral edge defines the interior opening, such that said corresponding surface area extends between at least a portion of the inboard peripheral edge and the outer peripheral edge.

7. The nasal dilator as in claim 1, further comprising at least one of a cover member corresponding to at least a portion of the engagement element, wherein the at least one of a cover member frames a portion of the decorative design element.

8. The nasal dilator as in claim 1, wherein the resilient element includes at least one spring finger extending outward from a common center.

\* \* \* \* \*